US010278905B1

(12) United States Patent
Byren et al.

(10) Patent No.: US 10,278,905 B1
(45) Date of Patent: May 7, 2019

(54) SPRAYABLE COMPOSITIONS CONTAINING METAL OXIDES

(71) Applicant: Johnson & Johnson Consumer Inc., Skillman, NJ (US)

(72) Inventors: David Scott Byren, Hoboken, NJ (US); Michael J. Fevola, Belle Mead, NJ (US); Jessica Leigh Ledingham, River Vale, NJ (US); Jeffrey Daniel Martin, Hillsborough, NJ (US); Bashar Oussama Salah, Plainsboro, NJ (US)

(73) Assignee: Johnson and Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/805,563

(22) Filed: Nov. 7, 2017

(51) Int. Cl.
| | |
|---|---|
| *A61K 8/27* | (2006.01) |
| *A61K 8/06* | (2006.01) |
| *A61K 8/02* | (2006.01) |
| *A61K 8/87* | (2006.01) |
| *A61Q 17/04* | (2006.01) |
| *A61Q 1/02* | (2006.01) |
| *A61K 8/81* | (2006.01) |

(52) U.S. Cl.
CPC .............. *A61K 8/06* (2013.01); *A61K 8/0245* (2013.01); *A61K 8/27* (2013.01); *A61K 8/8152* (2013.01); *A61K 8/87* (2013.01); *A61Q 1/02* (2013.01); *A61Q 17/04* (2013.01); *A61K 2800/594* (2013.01); *A61K 2800/622* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 8,158,714 B2 * | 4/2012 | Nair | C08F 220/18 524/497 |
| 9,144,535 B1 | 9/2015 | Daly et al. | |
| 9,144,536 B1 | 9/2015 | Daly et al. | |
| 9,713,587 B2 | 7/2017 | Nijakowski | |
| 2014/0178325 A1 * | 6/2014 | Martinez-Castro | A61K 8/8152 424/70.16 |
| 2015/0119525 A1 * | 4/2015 | Rabasco | C08G 18/10 524/591 |

FOREIGN PATENT DOCUMENTS

WO  WO 2008/117017  10/2008

OTHER PUBLICATIONS

Avalure™ Flex-6 Polymer Multifunctional Flexible Solution for Formulating High Performance Skin Care, Sun Care, Color Cosmetics, Lubrizol Technical Data Sheet, TDS-966, Jun. 12, 2015, pp. 1-5.
Mallory McMahon-Burleson, Ph.D., A New Multifunctional Polyurethane for Personal Care Formulations, IP.com No. IPCOM000243077D, The Lubrizol Corporation, Sep. 11, 2015, pp. 1-39.
VOLAREST™ FL, Acrylates/Beheneth-25 Methacrylate Copolymer, CRODA Inc. , Nov. 15, 2013, pp. 1-13.

* cited by examiner

*Primary Examiner* — Ernst V Arnold

(57) ABSTRACT

The present invention provides a composition comprising a high load of metal oxides that is phase stable and sprayable. It comprises a branched hydrophobically modified ethoxylated urethane copolymer and a hydrophobically modified alkali swellable emulsion copolymer comprising of one or more acrylate monomers and an ethoxylated associative comonomer.

18 Claims, 2 Drawing Sheets

SPRAYABLE COMPOSITIONS CONTAINING METAL OXIDES

BACKGROUND OF THE INVENTION

It is well known that prolonged exposure to ultraviolet (UV) radiation, especially from the sun, can lead to the formation of light dermatoses and erythemas, and increase the risk of skin cancers, such as melanoma. Exposure to UV radiation also accelerates skin aging, such as loss of skin elasticity and wrinkling.

For these reasons, sunscreen compositions are commonly used to provide photoprotection from the sun. Sunscreen compositions containing inorganic sunscreen agents, i.e., metal oxides like zinc oxide or titanium dioxide, are preferred by many consumers who desire mild products with a minimum of potentially irritating ingredients. Metal oxides, however, are difficult to formulate into sprayable compositions, a product form that is popular due to convenient application. As dense particles, metal oxides tend to settle in formulations, and are therefore difficult to suspend in dispersions over extended time periods, e.g. product shelf life. This is especially true for sunscreen compositions having little or no organic UV filter content, which require higher loads of metal oxides for adequate UV protection.

It has now been discovered that a composition comprising high levels of metal oxides that is both sprayable and stable may be prepared using a combination of a branched hydrophobically modified ethoxylated urethane copolymer ("HEUR") and a hydrophobically modified alkali swellable ("HASE") emulsion copolymer. Advantageously, the composition may be a sunscreen, and in certain embodiments is substantially free or completely free of organic UV filters.

SUMMARY OF THE INVENTION

The present invention provides a composition comprising: (a) at least about 10 weight percent of a metal oxide; (b) about 0.1 to about 5 weight percent of branched hydrophobically modified ethoxylated urethane copolymer; and (c) about 0.1 to about 5.5 weight percent of a hydrophobically modified alkali swellable emulsion copolymer comprising an ethoxylated associative comonomer and one or more acrylate monomers.

The invention further provides a composition comprising at least about 10 weight percent of a metal oxide having a viscosity less than 50,000 cP within a shear rate rage of 0.01 to 0.1 $s^{-1}$, and a loss tangent greater than 2.5 in an angular frequency range of 0.1 to 1 rad/s.

DETAILED DESCRIPTION OF THE INVENTION

Figure 1:
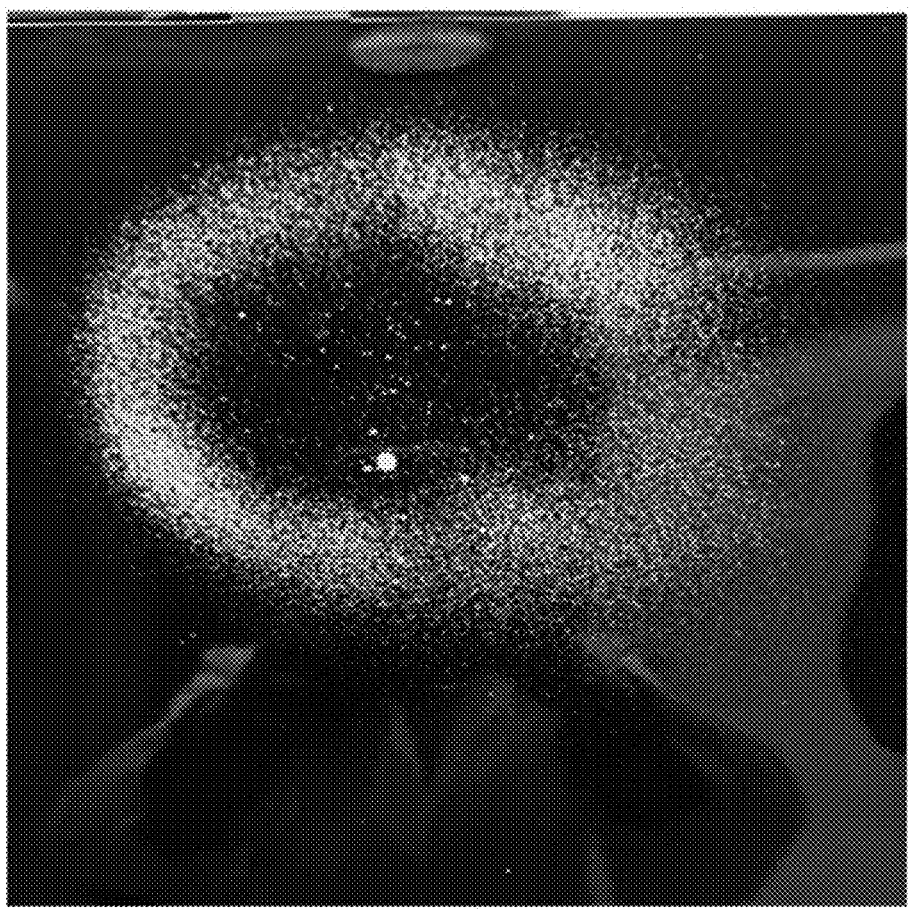
FIG. 1 shows the spray pattern of Composition 1 of Example 2.

Unless defined otherwise, all technical and scientific terms used herein have the same meaning as commonly understood by one of ordinary skill in the art to which the invention belongs. All publications, patent applications, patents, and other references mentioned herein are incorporated by reference.

Where applicable, chemicals are specified according to their INCI Name. Additional information, including definitions, suppliers, and trade names, can be found under the appropriate INCI monograph in the *International Cosmetic Ingredient Dictionary and Handbook*, 16th Edition published by the Personal Care Products Council, Washington D.C. Also available via the Personal Care Products Council On-Line INFOBASE (http://online.personalcarecouncl.org/jsp/Home.jsp).

As used herein, "topically applying" means directly spraying, wiping, laying on, or spreading on outer skin or the scalp, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "sunscreen composition" refers to a formulation (e.g. a lotion, spray, gel or other topical product) that absorbs and/or reflects some of the sun's ultraviolet (UV) radiation and thus helps protect against negative effects of sun exposure, e.g. sunburn, premature aging, etc.

As used herein, "color cosmetic" means a composition for application to the hair, nails and/or skin, especially the face, which contains at least about 0.01% and up to about 50% of pigment. Color cosmetics include, but are not limited to, foundations, concealers, primers, blush, mascara, eyeshadow, eyeliner, lipstick, nail polish and tinted moisturizers. The present invention is particularly suited for use with primers.

As used herein, "foundation" means a liquid, solid, or semi-solid cosmetic composition for imparting color to the skin, especially the face. It may be in the form of a lotion, cream, gel, serum, compact, stick, or paste.

As used herein, "concealer" means a liquid, paste, or semi-solid cosmetic composition for imparting color to the skin, containing a relatively high level of pigments having opacity, such as titanium dioxide, typically used prior to applying foundation, for example for concealing age or acne spots or scars.

As used herein, "primer" means a liquid, paste, or semi-solid cosmetic composition for application directly to the skin underneath foundations and/or concealers. Primers ease the application of foundation (or other skin care composition) onto the skin, even out skin tone, and increase the longevity of skin care compositions applied over the primer. Primers also may be used to smooth fine lines, such as around the mouth. A lip primer used underneath lipstick can maintain lip color and prevent feathering of the lipstick. Foundation primer used around the eye area can decrease creasing of eyeshadow. Use of a foundation primer may also decrease the amount of foundation required to achieve the same effect. Primers typically comprise waxes, polymers, and silicones.

As used herein, "cosmetically effective amount" means an amount of a physiologically active compound or composition sufficient for treating one or more conditions, but low enough to avoid serious side effects. The cosmetically effective amount of the compound or composition will vary with the condition being treated, the age and physical condition of the end user, the severity of the condition being treated/prevented, the duration of the treatment, the nature of other treatments, the specific compound or product/composition employed, the cosmetically-acceptable carrier utilized, and like factors.

As used herein, "cosmetically acceptable" means that the ingredients the term describes are suitable for use in contact with tissues (e.g., the skin) without undue toxicity, incompatibility, instability, irritation, allergic response, or the like.

As used herein, a "cosmetically acceptable active agent" is a compound (synthetic or natural) that has a cosmetic or therapeutic effect on the skin.

As used herein, "treatment or treating" refers to mitigating, reducing, preventing, improving, or eliminating the presence or signs of a condition or disorder.

In certain embodiments, the composition is phase stable. "Phase stability" as used herein, means the maintenance of interfacial stability or suspension stability or both at each of the temperatures 25° C., 40° C., and 50° C. for at least 2 weeks. "Interfacial stability" refers to stability against coalescence and coarsening of a discontinuous phase in a composition having two or more phases. "Suspension stability" refers to stability against creaming and/or sedimentation of a discontinuous phase, for example solids, suspended in continuous phase.

In one embodiment of the invention, the composition maintains both interfacial stability and suspension stability at each of the temperatures 25° C., 40° C., and 50° C. for at least 2 weeks. To assess such stability conditions, the composition may be filled into an appropriately sized vessel where it is fully visible, such as a clear 4 oz. glass jar.

The interfacial stability of the composition can be assessed visually and is considered unstable if at least two distinct, immiscible phases of the composition are observed, as well known in the art.

Also as known in the art, the suspension stability of the composition can be assessed visually or tactilely and is considered unstable if a distinct separation or gradient in color, opacity, grittiness, or other indicator of non-uniformity between different regions in a sample (i.e., top and bottom, or other different regions) is observed. The suspension stability of the composition can alternatively be assessed through, but not limited to, Brookfield viscosity and is considered unstable if there are significant changes in viscosity measurement (5 or 10 or 20% for example) between different regions in a sample (i.e., top and bottom or other different regions). Brookfield viscosity may be measured with a Brookfield Laboratory Viscometer from AMETEK Inc. (Middleboro, Mass.), using a setting, spindle, and speed appropriate for the composition's viscosity.

Overall phase stability may also be assessed by other techniques known in the art, for example significant changes in chemical composition as determined by analytical chemistry testing between different regions in a sample (i.e. top and bottom or other different regions).

Unless otherwise indicated, a percentage or concentration refers to a percentage or concentration by weight (i.e., % (W/W)). Unless stated otherwise, all ranges are inclusive of the endpoints, e.g., "from 4 to 9" includes the endpoints 4 and 9.

Metal Oxide

The composition comprises at least about 10 weight percent of a metal oxide. One or more than one metal oxide may be used.

In one embodiment, the composition comprises at least about 10 to about 30 weight percent of the metal oxide.

The metal oxide may for example be zinc oxide, titanium dioxide, doped zinc oxide, doped titanium dioxide, or mixtures thereof. Dopants are trace elements of other metal atoms incorporated into the crystal lattice of the primary metal oxide to modify its electrical or optical properties and may include aluminum, manganese, and iron.

In one embodiment, the metal oxide is zinc oxide. Commercially available zinc oxide sunscreens include MZX-3040TS from Tayca Corporation.

In another embodiment, the metal oxide comprises coated particles. The coating may comprise for example hydrophobic materials such as alkyl siloxanes (e.g. triethoxycaprylylsilane), silicones or metal salts of fatty acids.

In one embodiment, the metal oxide comprises particles having a diameter from about 0.01 micron to about 10 microns.

In one embodiment, the inorganic sunscreen may further comprise particulate doped zinc oxides as referred in U.S. Pat. Nos. 9,144,535, 9,144,536 and WO2008117017, incorporated herein by reference in their entirety. Such particulate zinc oxides comprise low levels of certain dopants at particular ratios and provide improved performance with respect to absorption in the UVA portion of the electromagnetic spectrum. The particulate zinc oxides comprise a cationic portion that in turn comprises about 99% by weight or more of a zinc portion. The cationic portion further comprises first and second dopant portions comprising metals such as manganese, iron, aluminum, and copper. The first and second dopant portions may be present in amounts of about 0.1% to about 0.75% by weight of the cationic portion. The particulate doped zinc oxides may further comprise additional metal cations, for example, cations of alkali metals, alkaline earth metals, other transition metals, as well as cations of metals such as gallium, germanium, gallium, indium, tin, antimony, thallium, lead, bismuth, and polonium, in small concentrations.

These doped zinc oxides may be made by various methods, such as by reducing oxide ores using, for example, carbon or other suitable reducing agents, and then re-oxidizing. Other suitable methods include wet chemical methods. One example of a wet chemical method includes mixing alkaline salt solutions of the various cations and causing ZnO to precipitate by reducing the pH using an acid such as oxalic or formic acid. A particularly suitable wet chemical method is the so-called "sol-gel" method.

In one embodiment, the composition is substantially free of organic UV filters. As used herein, "substantially free of" means the ingredient referred to is not directly and intentionally added to the formula. Preferably, "substantially free of" means containing less than about 1%, preferably less than about 0.5%, more preferably less than about 0.1% by weight of an ingredient.

In another embodiment, the composition is completely free of, i.e., contains no, organic UV filters.

In another embodiment, the composition comprises one or more organic UV filters.

As used herein, "organic UV filter" means an organic molecule capable of absorbing UV light, including: (i) aromatic compound conjugated with a carbonyl moiety substituted in the ortho- or para-position of the aromatic ring, and (ii) polymers made of organic chromophores attached to a polymer chain, either of which block or absorb ultraviolet (UV) light.

Traditional organic UV filters are aromatic, small molecules with molecular weight values<900 g/mol. Examples of organic non-polymeric UV filters include, but are not limited to: methoxycinnamate derivatives such as octyl methoxycinnamate and isoamyl methoxycinnamate; camphor derivatives such as 4-methyl benzylidene camphor, camphor benzalkonium methosulfate, ecamsule (Mexoryl® SX); terephthalylidene dicamphor sulfonic acid, and terephthalylidene dicamphor sulfonic acid; salicylate derivatives such as octyl salicylate, trolamine salicylate, ethylhexyl salicylate and homosalate; sulfonic acid derivatives such as phenylbenzimidazole sulfonic acid; benzone derivatives such as dioxybenzone, sulisobenzone, and oxybenzone; benzoic acid derivatives such as aminobenzoic acid and octyldimethyl para-amino benzoic acid; octocrylene and other β,β-diphenylacrylates; dioctyl butamido triazone; octyl triazone; avobenzone (butyl methoxydibenzoylmethane); drometrizole trisiloxane; menthyl anthranilate; triazone derivatives such as ethylhexyl triazone (Uvinul® T150); diethylhexyl butamido triazone (UVASorb® HEB); bis-ethylhexyloxyphenol methoxyphenyl triazine (Tinosorb® S), benzoate derivatives such as diethylamino hydroxybenzoyl hexyl benzoate (Uvinul® A Plus), benzotriazole derivatives such as drometrizole trisiloxane (Mexoryl® XL), methylene bis-benzotriazolyl tetramethylbutylphenol; tris-biphenyl triazine; (2-{4-[2-(4-Diethylamino-2-hydroxy-benzoyl)-benzoyl]-piperazine-1-carbonyl}-phenyl)-(4-diethylamino-2-hydroxy-phenyl)-methanone; merocyanine derivatives; bis(butylbenzoate) diaminotriazine aminopropylsiloxane; and bis-ethylhexyloxyphenol methoxyphenyl triazine, encapsulated in a polymer matrix.

Polymeric, organic UV filters are polymers made of organic chromophores attached to polymer chains, for instance a polysiloxane chain having for example an average molecular weight of >6000 Daltons. Examples of such polysiloxane UV filters include, without limitation Parsol® SLX and polysilicone-15. These polysiloxanes absorb in the UVB ($\lambda_{max}$=312 nm) part of the spectrum and are typically combined with UVA filters to achieve broad-spectrum protection.

The following table lists various commercially available organic UV filters.

| UV Filter | Other names | Coverage |
| --- | --- | --- |
| Benzophenone-3 | Oxybenzone or 2-hydroxy-4-methoxybenzophenone | UVA/B |
| Benzophenone-4 | Sulizobenzone or 2-hydroxy-4-methoxybenzophenone-5-sulfonic acid and its trihydrate | UVA/B |
| Benzophenone-5 | 2-hydroxy-4-methoxybenzophenone-5-sulfonic acid (benzophenone-5) and its sodium salt Sulizobenzone sodium Sodium hydroxymethoxybenzophenone sulfonate | UVA/B |
| Benzophenone-8 | Dioxybenzone or 2,2'-dihydroxy-4-methoxybenzophenone dioxybenzone (2-hydroxy-4-methoxyphenyl)(2-hydroxyphenyl)methanone methanone, (2-hydroxy-4-methoxyphenyl)(2-hydroxyphenyl) | UVA/B |
| 3-benzylidene camphor | 3-benzylidene camphor | UVB |
| Bis ethylhexyloxyphenol methoxyphenyl triazine | Tinosorb S or (1,3,5)-triazine-2,4-bisf{[4-(2-ethyl-hexyloxy)-2-hydroxy]-phenyl}-6-(4-methoxyphenyl) or anisotriazine | UVA/B |
| Butylmethoxy dibenzoyl methane | Avobenzone or 1-(4-tert-butylphenyl)-3-(4-methoxyphenyl) propane-1,3-dione | UVA |
| Camphor benzalkonium Methosulfate | Mexoryl SO or N,N,N-trimethy1-4-(2-oxoborn-3-ylidene-methyl) anilinium methyl sulphate | UVB |
| Diethylamino hydroxybenzoyl hexyl benzoate | Uvinul A plus or benzoic acid, 2-[-4-(diethylamino)-2-hydroxybenzoyl]-, hexylester | UVA |
| Diethylhexyl butamido triazone | UVASorb HEB or benzoic acid, 4,4-((6-((4-(((1,1-dimethylethyl) amino) carbonyl) phenyl) amino) 1,3,5-triazine-2,4-diyl) diimino) bis -(2-) ester) or dioctyl butamido triazone | UVB |
| Disodium phenyl dibenzimidazole tetrasulfonate | Neo Heliopan AP or monosodium salt of 2-2'-bis(1,4-phenylene)1H-benzimidazole-4,6-disulphonic acid) or bisimidazylate | UVA |
| Drometrizole trisiloxane | Mexoryl XL or phenol,2-(2H-benzotriazol-2-yl)-4-methy1-6-(2-methyl-3-(1,3,3,3-tetramethy1-1-(trimethylsilypoxy)-disiloxanyl)propyl) | UVA/B |
| Ethoxyethyl methoxycinnamate | Cinoxate | UVB |
| Ethylhexyl dimethylamino Benzoate | Padimate O Octyl dimethyl PABA Ethylhexyl dimethyl PABA | UVB |
| Ethylhexyl methoxycinnamate | OMC or octinoxate Octyl methoxycinnamate | UVB |
| Ethylhexyl salicylate | Octisalate 2-ethylhexyl salicylate Octyl salicylate | UVB |
| Ethylhexyl triazone | Uvinul T150 2,4,6-trianilino-(p-carbo-2'-ethylhexyl-1'oxy)-1,3,5-triazine Octyl triazone | UVB |
| Homosalate | 3,3,5-trimethylcyclohexyl 2-hydroxybenzoate Salicilato de homomentila | UVB |
| Isoamyl p-methoxycinnamate | Amiloxate Isopentyl-4-methoxycinnamate | UVB |

| UV Filter | Other names | Coverage |
| --- | --- | --- |
| Methyl anthranilate | Meradimate | UVA |
| 4-methylbenzylidene camphor | Enzacamene<br>3-(4'-methylbenxylidene)d-1 camphor<br>4 MBC | UVB |
| Methylene bis-benzotriazolyl tetramethylbutylphenol | Tinosorb M<br>2,2'-methylene-bis-6-(2H-benzotriazol-2yl)-4-(tetramethyl-butyl)-1,1,3,3-phenol | UVA/B |
| Octocrylene | 2-cyano-3,3-diphenyl acrylic acid, 2-ethylhexyl ester | UVB |
| Para aminobenzoic acid | PABA<br>4-aminobenzoic acid | UVB |
| PEG-25 PABA | Ethoxylated ethyl-4-aminobenzoate | UVB |
| Phenyl benzimidazole sulfonic acid | Neo Heliopan Hydro - Ensulizole<br>2-phenylbenzimidazole-5-sulphonic acid and its potassium, sodium, and triethanolamine salts<br>Potassium, Sodium, and TEA Phenylbenzimidazole sulfonate | UVB |
| Polyacrylamido methylbenzylidene Camphor | Mexoryl SW<br>Polymer of N-[(2 and 4)-[(2-oxoborn-3-ylidene)methyl]benzyl]acrylamide | UVB |
| Polysilicone-15 | Parsol SLX<br>Diethylbenzylidene malonate Dimethicone<br>Diethylmalonylbenzylidene Oxypropene dimethicone<br>Dimethicodiethylbenzalmalonate | UVB |
| Triethanolamine salicylate | Neo Heliopan TES<br>Trolamine salicylate | UVB |
| Terephtalydene dicamphor sulfonic acid | Mexoryl SX | UVA |
| Benzylidene camphor sulfonic acid | Alpha-(2-oxoborn-3-ylidene)-toluene-4-sulfonic acid and its salts | |

The SPF of the composition may be determined using the in-vivo "Colipa Method," known to those skilled in the sunscreen art. In this method, the minimum dose of solar-simulated ultraviolet radiation (UVR) required to induce a minimally perceptible erythema on human skin is determined for untreated skin and for the skin treated with the composition (erythema readings taken 24 hours after irradiation). The ratio of the dose of UV radiation needed to induce minimally perceptible erythema for the composition-protected skin (MEDp), divided by the dose required for a minimally perceptible erythema for unprotected skin (MEDu) results in the SPF value of the composition.

An irradiation apparatus used for SPF determinations is, for example, a Multiport Solar Simulator Model 601 (Solar Light Co., Philadelphia, Pa., USA) which consists of a 300 W Xenon lamp filtered with a UG11 1 mm thick filter and a WG320 1 mm filter (Schott Co., Philadelphia, Pa., USA) to allow exposure to UV between 240 and 800 nanometers.

Alternatively, the SPF of the composition may be determined using the USA FDA Final Rule test method, No. FDA 1978-N-0018, also known to those skilled in the sunscreen art.

In one embodiment, the composition has an SPF of at least about 15. In another embodiment, the composition has an SPF of at least about 25.

The composition may comprise one or more SPF boosters, such as styrene/acrylates copolymer. A commercially available styrene/acrylates copolymer is SUNSPHERES Powder from Dow Chemical.

Hydrophobically Modified Urethane Copolymer

The composition also contains about 0.1 to about 5 weight percent of a hydrophobically modified urethane copolymer comprising branched backbone, i.e. a branched hydrophobically modified ethoxylated urethane copolymer (HEUR). One or more than one branched hydrophobically modified ethoxylated urethane copolymer may be used.

Examples of HEURs useful in the invention include without limitation HEURs synthesized via 1) copolymerization of a diisocyanate comonomer, e.g., hexamethylene diisocyanate, isophorone diisocyante, with a PEG diol or diamine comonomer, and a polyfunctional comonomer (having 3 or more nucleophilic groups, e.g., hydroxyl, amino, etc.); examples include methyl glucosides, ethoxylated methyl glucosides (e.g. Methyl Gluceth-10), sugar alcohols (e.g. sorbitol), sugar alcohol anhydrides (e.g. sorbitan), pentaerythritol, trimethylolpropane, and 2) substitution of terminal positions (i.e. "end-capping") with a $C_{12}$ or higher linear, branched or cyclic hydrophobic chain end groups.

Preferably, the HEUR is Polyurethane-62, a copolymer of hexamethylene diisocyanate [diisocyante comonomer], PEG-200 [PEG diol], Methyl Gluceth-10 [polyfunctional comonomer], end-capped with Trideceth-6 and a fatty alcohol containing 16 to 20 carbons [hydrophobic chain end groups].

Polyurethane-62 is commercially available as AVALURE™ Flex-6 Polymer, an aqueous solution of polyurethane-62 and trideceth-6, from Lubrizol Advanced Materials, Inc.

Hydrophobically Modified Alkali Swellable Emulsion Copolymer

The composition also contains a hydrophobically modified alkali swellable emulsion (HASE) copolymer comprising one or more acrylate monomers and an ethoxylated associative comonomer. One or more than one hydrophobically modified alkali swellable emulsion copolymer may be used.

The composition contains about 0.1 to about 5.5 weight percent of the hydrophobically modified alkali swellable emulsion copolymer.

Acrylate monomers as used herein, refer to acrylic acid, methacrylic acid or one of their simple ($C_1$-$C_4$) esters and a $C_{16}$-$C_{24}$ ethoxylate (methacrylate) comonomer.

Ethoxylated associative comonomer as used herein is a monomer comprising an ethylenically-unsaturated polymerizable moiety covalently bound to a $C_{16}$-$C_{24}$ alkyl ethoxylate comprising 10-50 mols of ethylene oxide. Ethylenically-unsaturated polymerizable moieties include acryloyl, methacryloyl, acrylamido, methacrylamido, allyl, crotonoyl, and itaconoyl, with methacryloyl being preferred.

Examples of HASE copolymers include, without limitation, Acrylates/Beheneth-25 Methacrylate Copolymer, Acrylates/Steareth-25 Methacrylate Copolymer, Acrylates/Beheneth-25 Methacrylate/Steareth-30 Methacrylate Copolymer, Acrylates/Ceteareth-20 Methacrylate Crosspolymer, Acrylates/Ceteareth-20 Methacrylate Crosspolymer-2, Acrylates/Ceteth-20 Itaconate Copolymer, Acrylates/Ceteth-20 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Steareth-30 Methacrylate Copolymer, and Acrylates/Steareth-20 Methacrylate Crosspolymer.

In one embodiment, the HASE copolymer is acrylates/beheneth-25 methacrylate copolymer. Acrylates/beheneth-25 methacrylate copolymer is commercially available, for example, as VOLAREST FL from Croda Inc. or NOVETHIX L-10 from Lubrizol Advanced Materials, Inc.

In another embodiment, the HASE copolymer is acrylates/steareth-25 methacrylate copolymer. Acrylates/steareth-25 methacrylate copolymer is commercially available, for example, as ACULYN 22 from Rohm & Haas.

In certain embodiments, the HASE copolymer does not contain a crosslinking monomer, i.e. it is preferably a copolymer instead of a crosspolymer.

Topical Composition

The composition can be used by topically applying to a mammal, e.g., by the direct spraying, laying on, wiping or spreading of the composition on the skin, hair, or nails of a mammal, particularly a human.

The composition is in the form of an oil-in-water emulsion containing a continuous water phase and a discontinuous oil phase dispersed within the continuous water phase.

The composition may be prepared using mixing and blending methodology well known in the sunscreen and cosmetic art. In one embodiment, the composition is produced by preparing an oil phase by mixing the inorganic sunscreen with optional oil soluble or oil-miscible ingredients; and preparing a water phase, by mixing water and optional water-soluble or water-miscible ingredients. The oil phase and the water phase may then be mixed in a manner sufficient to disperse the oil phase substantially homogeneously in the water phase such that the water phase is continuous and the oil phase discontinuous.

The percentage by weight of water phase included in the compositions may range from about 30% to about 80%, such as from about 35% to about 75%, such as from about 40% to about 70%. The percentage by weight of water in the water phase may be about 60% or more, such as about 70% or more, such as about 90% or more.

In certain embodiments, the percentage by weight of oil phase in the composition is from about 20% to about 70%, such as from about 25% to about 65%, such as from about 30% to about 60%.

The composition may be combined with a "cosmetically-acceptable topical carrier," i.e., a carrier for topical use that capable of containing the other ingredients dispersed or dissolved therein, and possessing acceptable properties rendering it safe to use topically.

The cosmetically-acceptable topical carrier may optionally comprise a wide variety of additional oil-soluble materials and/or water-soluble materials conventionally used in compositions for use on skin, at their art-established levels. For example, surfactants, emulsifiers, pearlescent or opacifying agents, thickeners, emollients, conditioners, humectants, chelating agents, exfoliants, preservatives, pH adjusting agents, and additives that enhance the appearance, feel, or scent of the composition, such as colorants, fragrances, tactile modifiers, and the like, can be included.

Water soluble or water dispersible polymers may be added to the compositions. The water dispersible polymers are comprised of a water-insoluble polymer that is typically micronized and dispersed into a water carrier, possibly with the use of a surface active dispersing aid. The water dispersible polymers are capable of forming a film and improving water resistance of the compositions. Examples of water dispersible polymers include water dispersible polyurethanes, such as Baycusan® C1000 (Polyurethane-34), available from Bayer, Dow Corning® 2501 (Bis-PEG-18 Methyl Ether Dimethyl Silane), available from Dow Corning, Eastman AQ™ 38S (Polyester-5), available from Eastman Chemical, and Intelimer® 8600 (C8-22 Alkyl Acrylates/Methacrylic Acid Crosspolymer) available from Air Products.

Compositions of the present invention may include a film forming polymer to enhance film formation and provide some water resistance. A "film-forming polymer," as used herein means a polymer, when dissolved in the composition, permits a continuous or semi-continuous film to be formed when the composition is spread onto, e.g., smooth glass, and the liquid vehicle is allowed to evaporate. As such, the polymer should dry on the glass in predominantly continuous manner, rather than forming a plurality of discrete, island-like structures. Generally, the films formed by applying compositions on the skin according to embodiments of the invention described herein, are less than, on average, about 100 microns in thickness, such as less than about 50 microns.

Suitable film-forming polymers include natural polymers such as polysaccharides or proteins and synthetic polymers such as polyesters, polyacrylics, polyurethanes, vinyl polymers, polysulfonates, polyureas, polyoxazolines, and the like. Specific examples of film-forming polymers include, for example, acrylic homopolymers or copolymers with hydrophobic groups such as Acrylates/Octylacrylamide Copolymer including DERMACRYL 79 available from Akzo Chemical of Bridgewater, N.J.; Acrylates/Dimethicone Acrylate Copolymer available as X-22-8247D from Shin-Etsu of Japan; Hydrogenated Dimer Dilinoleyl/Dimethylcarbonate Copolymer, available from BASF Corp. as COSMEDIA DC; copolymer of vinylpyrrolidone and a long-chain alpha-olefin, such as those commercially available from Ashland Specialty Ingredients as GANEX V220; vinylpyrrolidone/tricontanyl copolymers available as GANEX WP660 also from Ashland; water-dispersible polyesters, including sulfopolyesters such those commercially available from Eastman Chemical as EASTMAN AQ 38S. In certain embodiments, the film-forming polymer is water insoluble, but is rendered soluble upon exposure to alkalinity in order to facilitate removal from the skin upon washing with soap.

The amount of film-forming polymer present in the composition may be from about 0.25% to about 15%, or from about 0.5% to about 10%, or from about 1% to about 3%.

Suitable emollients include mineral oils, petrolatum, vegetable oils (e.g. triglycerides such as caprylic/capric triglyceride), waxes and other mixtures of fatty esters, including but not limited to esters (e.g, isopropyl palmitate, isopropyl myristate, diisopropyl adipate, dibutyl adipate, dicaprylyl carbonate, C12-15 alkyl benzoate), silicone oils such as dimethicone, and alkanes such as isohexadecane.

Examples of suitable solvents include propylene glycol, 1,3-propanediol, butylene glycol, polyethylene glycol, polypropylene glycol, glycerol, 1,2,4-butanetriol, sorbitol esters, 1,2,6-hexanetriol, ethanol, isopropanol, and mixtures thereof.

In certain embodiments, the composition includes a pigment suitable for providing color or hiding power. The pigment may be one suitable for use in a color cosmetic product, including compositions for application to the hair, nails and/or skin, especially the face. Color cosmetic compositions include, but are not limited to, foundations, concealers, primers, blush, mascara, eyeshadow, eyeliner, lipstick, nail polish and tinted moisturizers. The pigment suitable for providing color or hiding power may be composed of iron oxides, including red and yellow iron oxides, titanium dioxide, ultramarine and chromium or chromium hydroxide colors, and mixtures thereof. The pigment may be a lake pigment, e.g. an organic dye such as azo, indigoid, triphenylmethane, anthraquinone, and xanthine dyes that are designated as D&C and FD&C blues, browns, greens, oranges, reds, yellows, etc., precipitated onto inert binders such as insoluble salts. Examples of lake pigments include Red #6, Red #7, Yellow #5, Violet #2 and Blue #1. The pigment may be an interference pigment. Examples of interference pigments include those containing mica substrates, bismuth oxychloride substrates, and silica substrates, for instance mica/bismuth oxychloride/iron oxide pigments commercially available as CHROMALITE pigments (BASF), titanium dioxide and/or iron oxides coated onto mica such as commercially available FLAMENCO pigments (BASF), mica/titanium dioxide/iron oxide pigments including commercially available KTZ pigments (Kobo products), CELLINI pearl pigments (BASF), and borosilicate-containing pigments such as REFLECKS pigments (BASF).

In one embodiment, the composition comprises a humectant such as butylene glycol or glycerin. The composition may comprise for example at least about 1.0 weight percent of a humectant.

In another embodiment, the composition has a pH of about 5.5 to about 9. The composition has a pH of about 6.5 to about 8. The composition may have a pH of about 7.

The composition may further comprise one or more other cosmetically acceptable active agents include for example anti-acne agents, shine control agents, anti-microbial agents, anti-inflammatory agents, anti-mycotic agents, anti-parasite agents, external analgesics, antioxidants, keratolytic agents, moisturizers, nutrients, vitamins, energy enhancers, antiperspiration agents, astringents, deodorants, firming agents, anti-callous agents, and agents for skin conditioning.

The amount of other cosmetically active agents may range from about 0.001% to about 20% by weight of the composition, e.g., about 0.005% to about 10% by weight of the composition, such as about 0.01% to about 5% by weight of the composition.

The cosmetically acceptable active agent may be selected for instance from D-panthenol carotenoids, ceramides, polyunsaturated fatty acids, essential fatty acids, enzymes such as laccase, enzyme inhibitors, minerals, steroids such as hydrocortisone, 2-dimethylaminoethanol, copper salts such as copper chloride, peptides like argireline, syn-ake and those containing copper, coenzyme Q10, amino acids such as proline, vitamins, lactobionic acid, acetyl-coenzyme A, niacin, riboflavin, thiamin, ribose, electron transporters such as NADH and FADH2, natural extracts such as from aloe vera, feverfew, oatmeal, dill, blackberry, princess tree, *Picia anomala*, and chicory, resorcinols such as 4-hexyl resorcinol, curcuminoids, sugar amines such as N-acetyl glucosamines, and derivatives and mixtures thereof.

Examples of vitamins include, but are not limited to, vitamin A, vitamin B's such as vitamin B3, vitamin B5, and vitamin B12, vitamin C, vitamin K, and different forms of vitamin E like alpha, beta, gamma or delta tocopherols or their mixtures, and derivatives thereof.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

In one embodiment, the composition is a sunscreen composition.

In another embodiment, the composition a color cosmetic.

Viscosity Test Method

In one embodiment of the invention, the composition has a viscosity less than 50,000 cps within a shear rate rage of 0.01 to 0.1 $s^{-1}$.

The viscosity of the composition is measured by the following method. A TA Instruments (New Castle, Del.) ARES G2 strain-controlled rheometer equipped with a Peltier temperature control system at 25° C. and a parallel plate geometry is used. A steady-state flow sweep is performed where the shear rate is increased from 0.01 to 1,000 $s^{-1}$, with four measuring points taken per decade. At each shear rate in the sweep, the rheometer monitors the torque over 10-second periods until either the torque does not fluctuate by more than five percent over two consecutive 10-second periods, or until the step time at that shear rate has exceeded 60 seconds. If the torque does not fluctuate by more than five percent in two consecutive 10-second periods, the measurement is considered to be at a steady state, and the torque is converted into a steady-state viscosity; if the torque has not stabilized in the 60-second step time, an average of the last 10 seconds is taken as the viscosity at that shear rate and the point is flagged as non-steady state.

Loss Tangent

In one embodiment, the composition has a loss tangent greater than 2.5 in an angular frequency range of 0.1 to 1 rad/s.

The loss tangent, also known as the solid/liquid balance, is calculated by dividing the loss modulus (G″) by the storage modulus (G′) in an oscillatory experiment. The loss tangent of the composition is measured by the following method. A TA Instruments (New Castle, Del.) ARES G2 strain-controlled rheometer equipped with a Peltier temperature control system at 25° C. and a parallel plate geometry is used. The linear viscoelastic regime for a sample is determined by performing a strain sweep oscillation step, where the strain amplitude is increased from 0.1 to 1000% strain at an angular frequency of one radian per second. The end of the linear viscoelastic regime is defined as the strain at which the storage modulus, G', deviates by more than 5% of its average low-strain plateau value. To determine the loss tangent versus frequency, a frequency sweep is performed by varying the angular frequency from 100 to 0.1 radians per second at a strain in the linear viscoelastic regime.

Sprayability

The composition of the invention is sprayable. "Sprayable" as used herein means the composition, when manually actuated or through pressurized release out of a dispensing mechanism, such as a bottle with pump spray nozzle or an aerosol can, creates a spray pattern evenly distributed and reproducible over an area of a defined shape (e.g. circle, annulus) and size.

It has been found that compositions having a viscosity less than 50,000 cP within a shear rate rage of 0.01 to 0.1 $s^{-1}$ and a loss tangent greater than 2.5 in an angular frequency range of 0.1 to 1 rad/s surprisingly provide excellent sprayability.

As set forth herein, such compositions may be formulated according to the invention by adding a branched hydrophobically modified urethane copolymer and hydrophobically modified alkali swellable emulsion copolymer comprising one or more acrylate monomers and an ethoxylated associate comonomer to the compositions in certain amounts.

Although the invention is not bound by theory, it is believed the combination of branched hydrophobically modified urethane copolymer and hydrophobically modified alkali swellable emulsion copolymer creates a composite network of amphiphilic polymers. The polymers assemble through an associative mechanism. In particular, hydrophobes on the HASE copolymer can associate with urethane copolymer hydrophobes, leading to intermolecular bridging associations between both polymers in aqueous solution. The bridging results in entanglement of the polymers and creation of the transient three-dimensional composite network, which allows for both stable suspension of the inorganic sunscreen in the composition, and good sprayability of composition.

The following non-limiting examples further illustrate the invention.

Example 1

The following composition according to the invention was made using the ingredients shown in Table 1 and in accordance with the following procedure. Unless otherwise indicated, all materials were added in the weight percent amounts as indicated, and the particular HEUR and HASE polymers used for each composition are also indicated in Table 1.

For the aqueous phase preparation, to an appropriately sized vessel equipped with a hotplate and over-head mechanical stirrer, Water was added and while mixing at an appropriate speed to generate a vortex, heated to 50° C. At temperature the HEUR polymer was slowly added and mixed until fully dissolved. Under adjusted mixing to maintain vortex, the HASE polymer was slowly added and mixed until fully dissolved. While continuing to mix and heat to 75° C., Butylene Glycol and Chlorphenesin were added and once fully incorporated Styrene/Acrylates Copolymer and Phenoxyethanol were added. The vessel was held at 75° C. for later emulsification step. Simultaneous to the aqueous phase preparation, for the oily phase preparation, to an appropriately sized vessel equipped with a hotplate and over-head mechanical stirrer, Isohexadecane, Polyhydroxystearic Acid, and Zinc Oxide; Triethoxycaprylylsilane were added in that order, and while mixing heated to 80° C. At temperature and under continued mixing, Cetyl Alcohol was added and mixed until fully melted. Phase was then mixed using a homogenzier, such as a Silverson high shear rotor/stator laboratory homogenizer, at 5000 rpm for at least 5 minutes, and returned to regular mixing and heated to 75° C., where it was maintained for the later emulsification step. Once both phases were complete and held at 75° C., while mixing the aqueous phase at high speed with a deep vortex, the oily phase was slowly added to the aqueous phase per standard emulsification technique, and held at 75° C. under continued mixing for at least 20 minutes. Composition was then cooled to under 40° C., where Silica was added and Water was added in q.s. to 100 wt %, where the batch was then allowed to mix until uniform before being discharged to an appropriate storage vessel.

TABLE 1

| INCI name | Activity {%} | wt. % |
|---|---|---|
| HEUR | | |
| Trideceth-6; Polyurethane 62 | 100 | 0.70 |
| HASE | | |
| Acrylates/Beheneth-25 Methacrylate Copolymer | 30 | 1.00 |
| Other | | |
| Butylene Glycol | 100 | 5.00 |
| Chlorphenesin | 100 | 0.27 |
| Styrene/Acrylates Copolymer | 87 | 5.55 |
| Phenoxyethanol | 100 | 0.50 |
| Isohexadecane | 100 | 20.00 |
| Polyhydroxystearic Acid | 100 | 2.00 |
| Zinc Oxide; Triethoxycaprylylsilane | 100 | 23.40 |
| Cetyl Alcohol | 100 | 0.50 |
| Silica | 100 | 1.00 |
| Water | 100 | Q.S. to 100% |

Example 2

The following inventive compositions (1-4) and comparative compositions (A-P) were made using the procedure and ingredients of Example 1, except that the amounts of the hydrophobically modified polyurethane ("HEUR") and/or hydrophobically modified alkali-swellable, alkali-soluble emulsion copolymer ("HASE") were changed, or one or both ingredients were removed and substituted with different polymers. All the compositions contained 22.5% by weight zinc oxide except for Composition 4, which contained 25% by weight zinc oxide.

For each composition, (i) the viscosity within the shear rate rage of 0.01 to 0.1 $s^{-1}$, ii) the loss tangent in the angular frequency range of 0.1 to 1 rad/s, and iii) whether the composition suspended the zinc oxide, assessed visually and/or with Brookfield viscosity at top and bottom of samples using the methods set forth above, at each of 25° C., 40° C., and 50° C. for a minimum of 2 weeks, were measured/tested.

The results are shown in Table 2.

TABLE 2

| Composition | HEUR INCI Name | HEUR Trade Name | wt. % | HASE INCI Name | HASE Trade name | wt. % | Viscosity less than 50,000 cps for Shear Rate Range 0.01-0.1 s$^{-1}$ (Pass/Fail) | Solid/Liquid Balance (loss tangent) greater than 2.5 within Angular Frequency Range 0.1-1 rad/s (Pass/Fail) | Formula Suspends Metal Oxide at Room Temp., 40 C., and 50 C. for a minimum of 2 wks. (Pass/Fail) |
|---|---|---|---|---|---|---|---|---|---|
| 1 | Trideceth-6; Polyurethane-62 | Avalure Flex-6 | 0.7 | Acrylates/Beheneth-25 Methacrylate Copolymer | Volarest FL-LQ | 1.0 | Pass | Pass | Pass |
| 2 | Trideceth-6; Polyurethane-62 | Avalure Flex-6 | 0.7 | Acrylates/Beheneth-25 Methacrylate Copolymer | Novethix L-10 Polymer | 1.0 | Pass | Pass | Pass |
| 3 | Trideceth-6; Polyurethane-62 | Avalure Flex-6 | 0.7 | Acrylates/Steareth-20 Methacrylate Copolymer | Aculyn 22 | 1.0 | Pass | Pass | Pass |
| 4 | Trideceth-6; Polyurethane-62 | Avalure Flex-6 | 0.7 | Acrylates/Beheneth-25 Methacrylate Copolymer | Volarest FL-LQ | 1.0 | Pass | Pass | Pass |
| A | Trideceth-6; Polyurethane-62 | Avalure Flex-6 | 5.0 | Acrylates/Beheneth-25 Methacrylate Copolymer | Volarest FL-LQ | 1.0 | Fail | Fail | Pass |
| B | Trideceth-6; Polyurethane-62 | Avalure Flex-6 | 0.7 | Acrylates/Beheneth-25 Methacrylate Copolymer | Volarest FL-LQ | 0.1 | Pass | Pass | Fail |
| C | Trideceth-6; Polyurethane-62 | Avalure Flex-6 | 0.1 | Acrylates/Beheneth-25 Methacrylate Copolymer | Volarest FL-LQ | 1.0 | Pass | Fail | Fail |
| D | Trideceth-6; Polyurethane 62 | Avalure Flex-6 | 0.7 | Acrylates/Beheneth-25 Methacrylate Copolymer | Volarest FL-LQ | 5.5 | Fail | Pass | Pass |
| E | Trideceth-6; Polyurethane-62 | Avalure Flex-6 | 0.7 | Acrylates/Steareth-20 Methacrylate Copolymer | Aculyn 22 | 2.0 | Pass | Pass | Fail |
| F | Trideceth-6; Polyurethane-62 | Avalure Flex-6 | 0.7 | Acrylates/Steareth 20 Methacrylate Crosspolymer | Aculyn 88 | 1.0 | Pass | Pass | Fail |
| G | Trideceth-6; Polyurethane-62 | Avalure Flex-6 | 0.7 | Acrylates/Steareth 20 Methacrylate Crosspolymer | Aculyn 88 | 2.0 | Pass | Pass | Fail |
| H | Trideceth-6; Polyurethane-62 | Avalure Flex-6 | 0.7 | Acrylates Copolymer | Carbopol Aqua SF-1 | 1.0 | Pass | Pass | Fail |
| I | Trideceth-6; Polyurethane-62 | Avalure Flex-6 | 0.7 | Acrylates Copolymer | Carbopol Aqua SF-1 | 2.0 | Pass | Fail | Fail |
| J | Trideceth-6; Polyurethane-62 | Avalure Flex-6 | 0.7 | Acrylates/C10-30 Alkyl Acrylate Crosspolymer | Carbopol ETD-2020 | 1.0 | Pass | Pass | Fail |
| K | Trideceth-6; Polyurethane-62 | Avalure Flex-6 | 0.7 | Acrylates/C10-30 Alkyl Acrylate Crosspolymer | Carbopol ETD-2020 | 2.0 | Pass | Pass | Fail |
| L | Trideceth-6; Polyurethane-62 | Avalure Flex-6 | 0.7 | Acrylates/C10-30 Alkyl Acrylate Crosspolymer | Pemulen TR-2 | 0.3 | Pass | Pass | Fail |
| M | Trideceth-6; Polyurethane-62 | Avalure Flex-6 | 0.7 | Acrylates/C10-30 Alkyl Acrylate Crosspolymer | Pemulen TR-2 | 1.0 | Pass | Pass | Fail |
| N | PEG-150/Stearyl | Aculyn 46 | 0.7 | Acrylates/Beheneth-25 | Volarest FL-LQ | 1.0 | Pass | Fail | Fail |

TABLE 2-continued

| | HEUR | | | HASE | | | Viscosity less than 50,000 cps for Shear Rate Range | Solid/Liquid Balance (loss tangent) greater than 2.5 within Angular Frequency Range | Formula Suspends Metal Oxide at Room Temp., 40 C., and 50 C. for a minimum of 2 wks. |
|---|---|---|---|---|---|---|---|---|---|
| Composition | INCI Name | Trade Name | wt. % | INCI Name | Trade name | wt. % | 0.01-0.1 s$^{-1}$ (Pass/Fail) | 0.1-1 rad/s (Pass/Fail) | (Pass/Fail) |
| O | Alcohol/ SMDI Copolymer Bis-C16-20 Isoalkoxy TMHDI/PEG-90 Copolymer | Rheoluxe 880 | 0.7 | Methacrylate Copolymer Acrylates/ Beheneth-25 Methacrylate Copolymer | Volarest FL-LQ | 1.0 | Untestable* | Untestable* | Fail |
| P | Bis-C16-20 Isoalkoxy TMHDI/PEG-90 Copolymer | Rheoluxe 880 | 2.3 | Acrylates/ Beheneth-25 Methacrylate Copolymer | Volarest FL-LQ | 1.0 | Pass | Fail | Fail |

Compositions 1 and N were tested as follows to assess their sprayability visually. Each composition was sprayed with a finger-actuated pump head with a 0.016″ insert that generates a "halo pattern." The compositions were sprayed upright at approximately 11 cm from a perpendicularly-oriented black surface target.

FIG. 1 shows the spray pattern of Composition 1 according to the invention. The spray pattern shows a fine spray on targeted delivery with an even distribution of droplets in the halo pattern (ie. clearly defined ring of spray around the targeted area).

Figure 2:
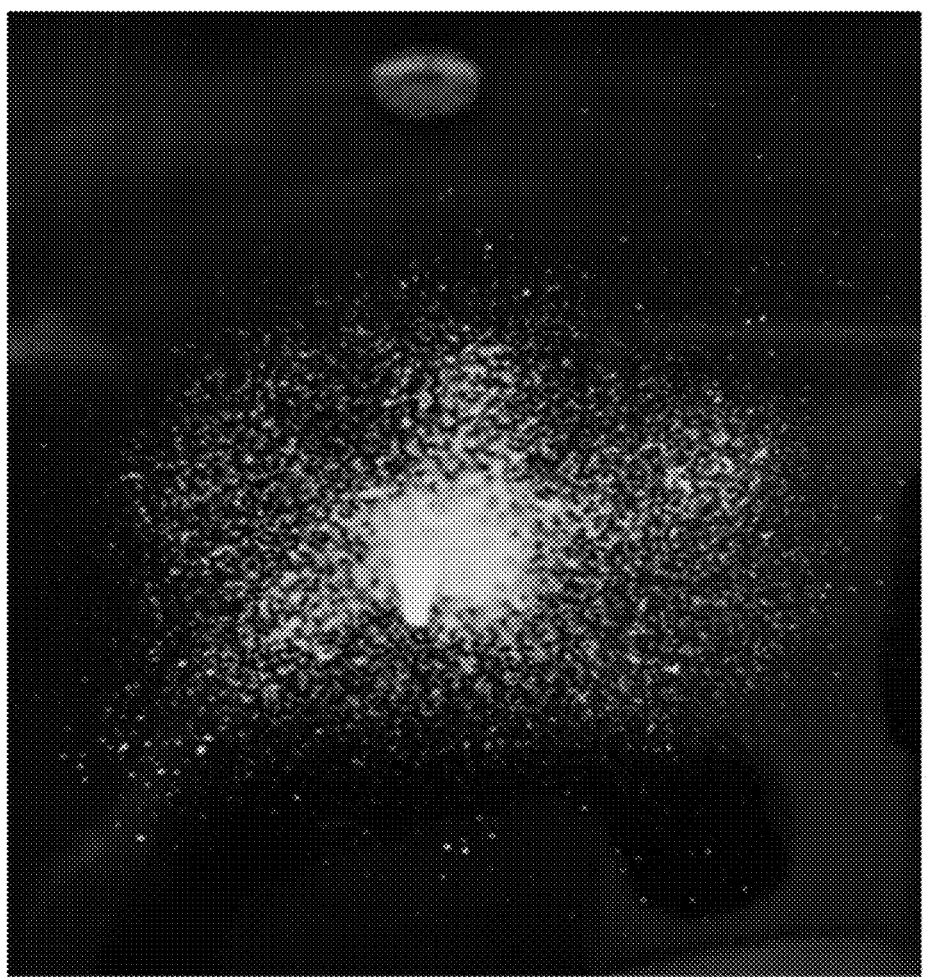
FIG. 2 shows the spray pattern of Composition N of Example 2.

In contrast, FIG. 2 shows the spray pattern of comparative Composition N, which did not form a halo, but instead deposited an agglomeration in the center of the target surface.

The invention claimed is:

1. A composition comprising:
    (a) at least about 10 weight percent of a metal oxide;
    (b) about 0.1 to about 5 weight percent of branched hydrophobically modified ethoxylated urethane copolymer; and
    (c) about 0.1 to about 5.5 weight percent of a hydrophobically modified alkali swellable emulsion copolymer comprising an ethoxylated associative comonomer and one or more acrylate monomers, wherein the branched hydrophobically modified ethoxylated urethane copolymer is a copolymer of hexamethylene diisocyanate, PEG-200, and Methyl Gluceth-10, end-capped with Trideceth-6 and a fatty alcohol containing 16 to 20 carbons.
2. The composition of claim 1, wherein the metal oxide is selected from the group consisting of zinc oxide, titanium dioxide and mixtures thereof.
3. The composition of claim 1, wherein the metal oxide comprises zinc oxide.
4. The composition of claim 3, wherein the zinc oxide comprises coated particles.
5. A composition comprising:
    (a) at least about 10 weight percent of a metal oxide;
    (b) about 0.1 to about 5 weight percent of branched hydrophobically modified ethoxylated urethane copolymer; and
    (c) about 0.1 to about 5.5 weight percent of a hydrophobically modified alkali swellable emulsion copolymer comprising an ethoxylated associative comonomer and one or more acrylate monomers, wherein the hydrophobically modified alkali swellable emulsion copolymer is selected from the group consisting of acrylates/beheneth-25 methacrylate copolymer, acrylates/steareth-25 methacrylate copolymer, and mixtures thereof.
6. The composition of claim 5, wherein the hydrophobically modified alkali-swellable emulsion copolymer comprises acrylates/beheneth-25 methacrylate copolymer.
7. The composition of claim 5, wherein the hydrophobically modified alkali-swellable emulsion copolymer comprises acrylates/steareth-25 methacrylate copolymer.
8. The composition of claim 1 substantially free of organic UV filters.
9. The composition of claim 1 comprising an organic UV filter.
10. A sunscreen composition according to claim 1.
11. A color cosmetic composition according to claim 1.
12. The composition of claim 5, wherein the metal oxide is selected from the group consisting of zinc oxide, titanium dioxide and mixtures thereof.
13. The composition of claim 5, wherein the metal oxide comprises zinc oxide.
14. The composition of claim 13, wherein the zinc oxide comprises coated particles.
15. The composition of claim 5 substantially free of organic UV filters.
16. The composition of claim 5 comprising an organic UV filter.
17. A sunscreen composition according to claim 5.
18. A color cosmetic composition according to claim 5.

* * * * *